United States Patent [19]

Niswender

[11] 4,048,298

[45] Sept. 13, 1977

[54] SOLID PHASE DOUBLE-ANTIBODY RADIOIMMUNOASSAY PROCEDURE

[75] Inventor: Gordon Dean Niswender, Fort Collins, Colo.

[73] Assignee: Rohm and Haas Company, Philadelphia, Pa.

[21] Appl. No.: 552,917

[22] Filed: Feb. 25, 1975

[51] Int. Cl.$^2$ .................. G01N 33/00; G21H 5/02
[52] U.S. Cl. .................. 424/1.5; 23/230 B; 424/12
[58] Field of Search ............... 424/1, 12, 1.5; 23/230

[56] References Cited

U.S. PATENT DOCUMENTS

| | | | |
|---|---|---|---|
| 3,790,663 | 2/1974 | Garrison et al. | 424/12 |
| 3,857,931 | 12/1974 | Hager | 424/12 |
| 3,904,367 | 9/1975 | Golibersuch | 23/230 B |

OTHER PUBLICATIONS

Goodfriend et al., Immunochemistry, vol. 6, No. 3, May, 1969, pp. 481–484.
Medgley et al., Acta Endocrinologica Supplementum, No. 142, 1969, pp. 247–256.
Donini et al., Acta Endocrinologica Supplementum, No. 142, 1969, pp. 257–278.
Salmon et al., The Journal of Immunology, vol. 104, No. 3, Mar. 1970, pp. 665–672.

Primary Examiner—Edward A. Miller
Assistant Examiner—Christine M. Nucker
Attorney, Agent, or Firm—Terence P. Strobaugh; Carl A. Castellan; George W. F. Simmons

[57] ABSTRACT

The present invention is concerned with the radioimmunoassay (RIA) procedure for assaying body fluid content of an antigenic substance which may either be an antigen itself or a hapten capable of being converted, such as by means of reaction with a protein, to an antigenic material. The present invention is concerned with a novel and improved modification of a double-antibody RIA technique in which there is a first antibody that is specific to the antigenic substance suspected to be present in a body fluid from which the assay is intended. The second antibody, however, is not specific to the antigenic substance or analyte, but is an antibody against the first antibody.

In accordance with the present invention, the second antibody may be covalently bonded to a water-insoluble organic polymeric substance, such as cellulose or other polysaccharide, a vinyl addition polymer or condensation polymer, such as an aminoplast or a polyester, or a water-insoluble inorganic substance of polymeric nature, such as glass or silicone resins or the second antibody may be adsorbed to the surface of a solid support, such as polystyrene or polypropylene. The antigenic substance, that is, the analyte to be assayed, hereinafter sometimes referred to broadly as a "ligand", may be a protein or a polypeptide, or it may be a vitamin, a drug, a glandular extract or secretion, such as a hormone of steroid or other type.

10 Claims, No Drawings

SOLID PHASE DOUBLE-ANTIBODY RADIOIMMUNOASSAY PROCEDURE

DESCRIPTION OF THE INVENTION

For the purpose of the specification and claims herein, the term "antigenic ligand" (or "antigenic analyte") is intended to be generic to (1) an antigen per se and (2) a hapten, which latter is not per se antigenic, but can be combined with an antigenic carrier, such as a protein, to thereby produce a hapten-bound antigenic carrier which, on introduction into the blood stream of a vertebrate, produces an antibody which is specific for the hapten.

The present invention is concerned with a double-antibody RIA technique which is modified by replacing the dissolved second antibody heretofore used for forming a macro-molecular agglomerate (that can be separated by centrifuging) with the first antibody on which labeled and unlabeled (if any is present) antigenic ligand are bound, with an insolubilized antibody obtained by (1) covalently coupling the soluble second antibody with an insoluble polymeric substance, (2) converting the soluble second antibody to an insoluble polymerized form, such as by reaction with an insolubilizing agent, such as an aldehyde, e.g., formaldehyde or glutaraldehyde, an alkyl haloformate, e.g., ethylchloroformate, (3) or physical entrapment of particles of the second antibody in the spores of a gel polymer e.g., in a cross-linked polyacrylamide or (4) by physical adsorption on an insoluble polymeric substance, such as any insoluble polymer, linear or cross-linked, of an ethylenically unsaturated monomer having one or more $H_2C = C=$ groups, e.g., polystyrene, polypropylene. The insolubilized polymer and/or the insolubilized antibody may be in particulate or other form such as self-supporting sheet or film or a container, such as a vial or test tube, or a film or layer on the inside wall of such a container. The term "receptor" may sometimes be applied herein broadly to an antibody developed immunologically from an antigenic material which antibody has sites which bind the respective antigenic material to the antibody in the so-called "lock-and-key" manner.

In the previous double-antibody technique, the sample of body fluid containing antigenic ligand to be assayed is mixed with an antibody or receptor (specific to the ligand or to a characteristic part of a derivative of the ligand molecule) as well as a corresponding radioactive isotope-labeled ligand, or analyte and/or a corresponding radioactive isotope-labeled ligand derivative. The unlabeled and labeled ligand compete for sites on the antibody. A certain time of incubation is allowed for such competitive reaction and thereafter the second antibody is added to agglomerate the first antibody to enable separation by centrifugation. The incubation may proceed until equilibrium is reached before addition of the second antibody; however, it is not always essential to reach equilibrium before such addition if the time of incubation is adequate to attain sufficient binding of labeled and unlabeled ligand to produce accurate results and a corresponding incubation time is used for standards of known concentration for preparing a standard curve against which the radioactivity is determined in conventional manner, such as by a gamma-counter or a liquid scintillation-counter.

In the double-antibody technique with which the present invention is concerned, the second antibody is one that is not specific for the ligand to be assayed, that is, it does not bind the ligand, and it is prepared by immunization of a different animal than the one in which the first antibody is prepared so that the two antibodies, when brought into contact, agglomerate and may be separated by centrifugation. Both such antibodies are water-soluble in character, but the second antibody in effect immobilizes, insolubilizes, or "precipitates" the first because the coreacted first- and second-antibody complex necessarily has a water-insoluble conformation by virtue of the previous attachment of the second antibody component to a water-insoluble polymeric substrate, thereby forming, in effect, a solid-phase second antibody. The first antibody is generally obtained by immunization of a rabbit with the particular antigenic ligand against which the antibody is to be specific. Of course, other animals could be used, such as hamsters, guinea pigs, dogs, cats, but as a matter of practice, convenience and cost, except in special cases, the rabbit is most commonly employed. The second antibody is prepared in a different animal than the one in which the first is developed, and is not specific to the ligand to be assayed. Most conveniently, the second antibody is obtained by immunization technique from an animal other than that in which the first antibody is obtained using, as the immunizing agent, the appropriate protein fraction from the serum (e.g., gamma-globulin) from the animal from which the first antibody is obtained. For example, when a rabbit is used to prepare the first antibody, a goat, sheep, hamster, guinea pig, dog, pig, cow, or horse may be injected with the appropriate protein fraction from the rabbit for the development of a second antibody which is specific to the protein fraction containing the first antibody and agglomerates with it when mixed with it in aqueous solution and is separated by centrifugation.

Among advantages of the double-antibody technique is the fact that the second antibody is specific to the first but not to the proteinaceous material present in the body fluid and originating from the animal from which the body fluid is taken for assay. Thus, when assaying a human body fluid, the second antibody does not agglomerate protein therein of human origin that may be present in the human body fluid in which the ligand is to be measured. Such human body fluid may be blood, blood serum, blood plasma, urine, lymph, bile, spinal fluid, saliva or other glandular secretions or extracts. The technique may be employed for assaying ligands in fluids from other animals than the human being.

The great advantage of the present method is that the antibodies are firmly attached to an insoluble carrier and that the labeled protein, which reacts with and is bound to the antibodies in the determination, can thus be easily separated from the unbound labeled protein, e.g., by simple settling, centrifugation, or filtrations, the separation being insensitive to variations in the salt and protein concentrations of the liquid within physiological limits.

In the double-antibody procedure heretofore employed, both antibodies have been soluble in the aqueous body fluid containing the antigenic ligand, i.e., antigen or hapten, to be assayed. The addition, to the first antibody (carrying the labeled and unlabeled ligand or antigen), of the second antibody which is not specific to the ligand or antigen to be assayed but is specific to the first antibody results, during a subsequent incubation, in a mutual agglomeration of the first and second antibodies to a product of sufficient molecular size to be capable of separation by centrifugation.

In accordance with the present invention, the soluble second antibody is replaced by an insolubilized second antibody obtained by attaching the soluble second antibody to a water-insoluble polymeric substance. This polymeric substance may be in granular or in finely-divided form. Alternatively it may take the form of a film or sheet; again, it may take the form of a container, e.g., a vial or test tube, or even a coating in such a container.

One of the advantages of using an insolubilized second antibody is that the precipitation of the first antibody thereby is considerably more efficient and therefore requires a shorter incubation time. Another advantage is that the second antibody is specific to the protein fraction containing the first antibody and does not precipitate the native protein in the body fluid being tested. In the case of a human body fluid, the proteinaceous content derived from the human being, such as human gamma-globulin, is not precipitated by the second antibody when the latter is added to the mixture containing the antigenic ligand (i.e., antigen or hapten), labeled antigenic ligand and the first antibody to which the labeled and unlabeled antigenic ligand has been bound.

Stated somewhat differently, the advantages of insolubilizing a second or precipitating antiserum are:

1. A second or precipitating antiserum is universal for all first antisera raised in the same specie, e.g., anti-rabbit gamma-globulin (ARGG) is useful for any rabbit antiserum.
2. A second or precipitating antiserum is concentration independent, i.e., an excess may be added without detrimental results, whereas a first antiserum is concentration dependent.
3. Immobilization of the second antibody before contacting it with the first dissolved antibody avoids the extended period of time needed for the complexing of two soluble antibodies to render them insoluble and separable by centrifugation, thereby resulting in a more rapid separation of bound from free antigen.

The modified double-antibody technique of the present invention may be applied to the determination or assay of antigenic ligands of numerous types. Numerous antigenic ligands have been determined to bind in the lock-and-key manner to a suitable antibody (obtained by immunization techniques) which, as stated hereinbefore, may be generically termed a "receptor". When a substance does not per se develop an antibody in an animal, it is termed a "hapten" and frequently it can be covalently bonded to an antigenic carrier, such as a protein,, to form a hapten/protein conjugate which serves as an antigenic ligand and, by immunization technique, is capable of developing an antibody or receptor which shows specificity toward the hapten portion of the conjugate.

Any ligand may be employed for which an appropriate receptor may be found having satisfactory specificity for the ligand. The recent literature contains an increasing number of reports of receptors for an increasingly wide variety of biologically active materials. Compounds for which antibodies or receptors can be provided range from simple phenylalkylamines, e.g., amphetamine, to very high molecular weight polymers, e.g., proteins.

A radioactive derivative of the ligand or antigen to be assayed is produced for use in the assay. A first antibody (or receptor) against the ligand or antigen is prepared by immunologic procedures and a second antibody (against the first antibody) is produced in a different animal by immunization procedures and the second antibody is thereafter combined with a water-insoluble polymeric substance.

The water-insoluble polymeric carrier to which the second antibody is bound may be any polymeric substance which has a suitable reactive group. The most important reactive groups are hydroxyl, carboxyl and primary or secondary amine groups. Examples of plymeric material containing hydroxyl groups include cellulose, microcrystalline cellulose, and various water-insoluble derivatives of cellulose including ethyl cellulose acetate; also crosslinked polyhydroxy compounds such as carbohydrates, sugar alcohols, including dextran, starch, dextrin and other polysaccharides as well as water-insoluble polymers, whether crosslinked or not, of monoethylenically unsaturated molecules such as acrylic and methacrylic acid esters including those esters formed with alcohols having from 1 to 18 carbon atoms, e.g., methyl acrylate, methyl methacrylate, ethyl acrylate or methacrylate, butyl acrylate or methacrylate, 2-ethylhexyl acrylate or methacrylate, dodecyl acrylate or methacrylate, and octadecyl acrylate or methacrylate, acrylonitrile, styrene, vinyl acetate, ethylene, propylene, vinyl chloride, vinylidine chloride, copolymerized with each other and also copolymerized with hydroxyethyl acrylate, hydroxyethyl methacrylate, glyceryl monoacrylate, glyceryl monomethacrylate, and other hydroxyl-containing comonomers. In copolymers containing vinyl acetate, the hydroxyl group may be obtained by partial hydrolysis. The various monomers mentioned above may be copolymerized with monoethylenically unsaturated acids, such as acrylic acid, methacrylic acid, maleic acid, itaconic acid, to introduce carboxyl groups. Similarly, primary and secondary amine groups may be obtained by copolymerization with amino alkyl esters of acrylic or methacrylic acid, especially 2-aminoethyl acrylate or methacrylate. The reactive group-containing copolymers may be crosslinked by inclusion of a substantial amount of a polyethylenically unsaturated monomer, such as from 1 to 20% or more by weight of ethylene glycol dimethacrylate, divinylbenzene, diallyl phthalate, thrimethylol propane trimethacrylate and N,N'-ethylene-bis-methacrylamide.

Depending upon the particular antigenic ligand or analyte to be assayed, the labeled product may contain any one of numerous radioactive substituents, such as iodine $131_I$, $125_I$, $14_C$, $57_{Co}$, $75_{Se}$, $59_{Fe}$ or tritium ($^3H$). Depending upon the particular radioactive substituent present in the labeled antigen, the determination of the radioactive content either bound in the precipitated material or in the free material after separation of the precipitated double-antibody material from the free soluble material, may be carried out with conventional equipment; such as a gamma-counter or a liquid scintillation-counter.

Among antigenic ligands which are drugs, will be compounds which act as narcotics, hypnotics, sedatives, analgesics, antipyretics, anaesthetics, psychotogenic drugs, muscle relaxants, nervous system stimulants, anticholinesterase agents, parasympathomimetic agents, sympathomimetic agents, α-adrenergic blocking agents, antiadrenergic agents, ganglionic stimulating and blocking agents, neuromuscular agents, histamines, antihistamines, 5-hydroxytryptamine and antagonists, cardiovascular drugs, antiarrhythmic drugs, antihypertensive agents, vasodilator drugs, diuretics, pesticides (fungicides, antihelminthics, insecticides, ectoparasiticides, etc.), antimalarial drugs, antibiotics, antimetabolites, hormones, vitamins, sugars, thyroid and antithyroid drugs, corticosteroids, insulin, oral hypoglemic drugs, tumor cells, bacterial and viral proteins, toxins, blood proteins, and their metabolities.

(A drug is any chemical agent that affects living protoplasm. (Goodman & Gilman, The Pharmacological Basis of Therapeutics, 3rd ed., Macmillan, New York (1965).) A narcotic is any agent that produces sleep as well as analgesia.)

Included among such drugs and agents are alkaloids, steriods, polypeptides and proteins, prostaglandins, catecholamines, xanthines, arylakylamines, heterocyclics, e.g., thiazines, piperazines, indoles, and thiazoles, amino acids, etc.

Other antigenic ligands of interest besides drugs are industrial pollutants, flavoring agents, food additives, e.g., preservatives, and food contaminants.

Broadly, the antigenic ligands will be organic compounds of from 100 to 100,000 molecular weight, usually of from about 125 to 40,000 molecular weight, more usually 125 to 20,000 molecular weight. They will usually have from about 8 to 5,000 carbon atoms and from about 1 to 3,500 heteroatoms.

A substantial portion of the antigenic ligands will be monomers or low order polymers, which will have molecular weights in the range of about 100 to 2,000 more usually 125 to 1,000. Another significant portion of the antigenic ligands will be polymers (compounds having a recurring group) which will have molecular weights in the range of from about 750 to 100,000, usually from about 2,000 to 60,000, more usually 2,000 to 50,000. For polymers of varying molecular weight, weight average molecular weight is intended.

In some instances, high molecular weight materials will be of interest. For example, blood proteins will generally be in excess of 100,000 molecular weight. In the case lipoproteins, the molecular weight will be in the range of 3 million to 20 million. The globulins, albumins and fibrinogens will be in the range of 100,000 to 1,000,000.

The antigenic ligands will normally be composed of carbon hydrogen, nitrogen, oxygen, sulfur, phosphorus, halogen, and metals, primarily as their cations, such as the alkali and alkaline earth metals and the metals of Groups IB, IIB, VIIB, and VIIIB, particularly the third row of the periodic chart. Most usually, the ligands will be composed primarily of carbon, hydrogen, nitrogen, oxygen and sulfur.

Structurally, the antigenic ligands may be monomers or polymers, acyclic, mono or polycyclic, having carbocyclic or heterocyclic rings. They may have a wide variety of functionalities, such as halo, oxocarbonyl, nonoxocarbonyl, amino, oxy (hydroxy, aryloxy, alyloxy and cycloallyloxy ["alyl" intends a monovalent aliphatic radical]), thiooxy, dithio, hydrazo, and combinations thereof.

The antigenic ligands may be divided into two different categories, based on their biological relationship to the receptor. The first category is antigens, which when introduced into the bloodstream of a vertebrate, result in the formation of antibodies. The second category is haptens; substances which can be bound to an antigenic carrier; introduction of the resulting hapten bound antigenic carrier into the bloodstream of a vertebrate, elicits formation of antibodies specific for the hapten.

Of course, biological substances which are native to one species and have naturally occurring receptors in that species, may also be haptens when bonded to a protein and introduced into an animal of the same or a different species. Therefore, the classification is somewhat arbitrary in that the ligand may be an antigen as to one species, a hapten as to another species, and may have naturally occurring receptors in a third species.

Antigens are for the most part protein or polysaccharide in nature and foreign to the animal into which they are injected.

The most important body of antigenic ligands for the purposes of the invention are the haptens. "Substances which on injection do not give rise to antibodies, but which are able to react with antibodies specifically to produce either precipitation or to inhibit precipitation have been termed haptens. This definition has been used to include not only the simple chemical substances which are determinants of specificity when conjugated to protein, and which inhibit precipitation, but also substances obtained from natural sources such as the pneumococcal type specific polysaccharides and dextran which are not antigenic in the rabbit on primary injection." Kabat, et al, Experimental Immunochemistry, Charles C. Thomas, Springfield, Ill. (1967). In the following discussion the term hapten will be confined to groups artificially introduced into antigenic carriers which promote the formation of antibodies to those groups.

The antigenic ligands may also be categorized by the chemical families which have become accepted in the literature. In some cases, included in the family for the purpose of this invention, will be those physiomimetic substances which are similar in structure to a part of the naturally occurring structure and either mimic or inhibit the physiological properties of the natural substances. Also, groups of synthetic substances will be included, such as the barbiturates and amphetamines. In addition, any of these compounds may be modified for linking to the enzyme at a site that may cause all biological activity to be destroyed. Other structural modifications may be made for the ease of synthesis or control of the characteristics of the antibody. These modified compounds are referred to as antigenic ligand counterfeits.

A general category of antigenic ligands of particular interest are drugs and chemically altered compounds, as well as the metabolites of such compounds. The interest in assaying for drugs varies widely, from determining whether individuals have been taking a specific illicit drug, or have such drug in their possession, to determining what drug has been administered or the concentration of the drug in a specific biological fluid.

In the subject invention, for the most part, the antibodies or receptors will be macromolecules which have sites which recognize specific structures. The recognition of the specific structures will be based on Van der Waals forces, which provide a specific spatial environment which maximizes the Van der Waals forces; dipole interactions, either by permanent or induced dipoles; hydrogen and ionic bonding; coordinate covalent bonding; and hydrophobic bonding. For a detailed discussion of mechanisms by which receptors bind ligands, see Goldstein, et al., Principles of Drug Action, Harper and Rowe, New York, 1968.

The macromolecules of greatest interest are proteins and nucleic acids which are found in cell membranes, blood, and other biological fluids. These compounds include enzymes, antibodies, ribonucleic acid (RNA) and deoxyribonucleic acid (DNA) and natural receptors.

The most convenient group of proteins for use in the subject invention are antibodies. These materials are conveniently used in the analysis of the category of ligands referred to a haptens. Antibodies are produced by introducing an immunogenic substance into the bloodstream of a living animal. The response to the introduction of the immunogenic substance for antigen is the production of antibodies which act to coat the antigen and detoxify it or precipitate it from solution. The protein forms a coat which is geometrically arranged so as to have the antigen fit the spatial arrangement of the protein. This has been analogised to a lock and key. The interaction is normally reversible, in that the antigen is subject to displacement or removal by various means without destruction of the receptor site.

There are many materials which are antigens and will produce an immunogenic response by being introduced into the bloodstream of a vertebrate.

However, a number of materials of interest are not antigens, but are haptens, and in that situation, an extra step in preparing the antibody is required. This method of preparing antibodies with materials other than antigens is well known and may be found in Microbiology, Hoeber Medical Division, Harper and Rowe, 1969. See also, Landsteiner, Specificity of Serological Reactions, Dover Publications, N.Y. 1962; Kabat, et. al., Experimental Immunochemistry, Charles C. Thomas, Springfield, Ill., 1967; and Williams et al, Methods in Immunology and Immunochemistry, Vol. I, Academic Press, New York, 1967.

The hapten which is to be assayed is bonded to a protein by any convenient means and the modified protein introduced into the bloodstream. The same type of bonding groups used with the enzyme attachment to the ligand may be employed. The antibodies which form will include groups of antibodies which are shaped to fit the foreign moiety bonded to the protein. Therefore, antibodies are obtained which are specific to the compound or moiety bonded to the protein. By careful separation techniques, the antibodies primarily concerned with the moiety in question, can be concentrated so as to provide an antibody composition which is primarily related to the specific moiety which was bonded to the protein.

Any suitable method may be employed for covalently bonding the second antibody to the water-insoluble polymeric material. Procedures for doing so may follow those disclosed in any of the following U.S. Pat. Nos.: 3,555,143, 3,652,761, 3,645,852, 3,830,699, 3,788,948, 3,775,253, 3,654,090.

The following procedure is illustrative of the present invention. It is to be understood that the invention as so exemplified is not to be limited to the particular examples given hereafter.

EXAMPLE 1

For RIA determination of human thyroid stimulating hormone (hTSH), the following solutions, blood sera, and solid phase second antibody conjugate are used;

A. 0.01 M Phosphate buffer solution (PBS) which contains 0.68 g $KH_2PO_4$ and 0.71 g. anhydrous $Na_2HPO_4$ in in one liter of water herein referred to as Buffer A.

B. The same solution as in A except it also contains 1.46 g. (0.05 M) per liter of ethylenediaminetetraacetic acid herein referred to as Buffer B.

C. A first antibody serum against hTSH obtained from the blood serum of a rabbit that has been injected with hTSH.

D. Normal rabbit serum obtained from a rabbit which has not been inoculated with antigen, e.g. hTSH, to be assayed.

E. Normal rabbit serum diluted by mixing 1 part of volume of serum in D above with 100 parts by volume of Buffer B.

F. A solution of the first antibody in C above at a dilution of 1 part by volume per 1000 obtained by diluting 1 part of antibody solution C above to 100 parts with Buffer B solution and then diluting 1 ml. of the resulting diluted solution with 9 ml. of the diluted solution obtained in E. above.

G. A solution in Buffer A of hTSH tagged by iodination with $^{125}I$. The solution of $^{125}I$-hTSH has a gamma ray radioactivity of 30,000 to 50,000 counts per minutes.

H. A second antibody serum obtained from the blood serum of a sheet injected with the gamma-globulin of a normal rabbit, i.e., one that has not been inoculated with hTSH.

I. Human blood serum taken from a person whose TSH level is to be determined.

J. Solid phase second antibody (H) covalently bonded to microcrystalline cellulose powder obtained from part B. of Example A hereinbelow.

a. In the prior procedure using both antibodies in soluble form, the following steps are employed:

1. A mixture is made of 50 microliters of antibody solution F. with 200 microliters of human blood serum I. to be tested and 250 microliters of the EDTA-containing phosphate buffer solution B.

2. This mixture is incubated at room temperature for 12 to 24 hours.

3. Then 100 microliters of the radioactive $^{125}I$-TSH solution G. hereinabove is added.

4. The mixture is incubated another 12 to 24 hours at room temperature.

5. Thereupon, 400 microliters of Buffer A containing 5.3 mg. of the second antibody serum H is added.

6. The resulting solution is incubated for 24 to 48 hours at room temperature.

7. Thereafter, the product is centrifuged at 800X g for 30 minutes. The solid residue from the centrifuging is washed two times with 0.01 M phosphate buffer solution (Buffer A) centrifuging after each washing.

8. The resulting solid product is then subjected to radioactivity detection as by means of a gamma-counter.

b. The procedure of the present example is identical to that described in part a) above through Step 4 — the second stage of incubation. Thereafter, in Step 5, 400 microliters of Buffer A containing, dispersed therein, 32 mg. of solid phase second antibody (J. above) is added and this mixture (Step 6) is incubated for one hour, agitating after the first 30 minutes. Then, (in Step 7) 3 ml. of the 0.01 M phosphate buffer solution (Buffer A) is added and the mixture is centrifuged for 5 minutes at 800X g. Thereafter, in Step 8, the solid residue is subjected to radioactivity detection as by a gamma counter.

NOTE: The solid phase second antibody used hereinabove is obtained in the following fashion:

EXAMPLE A

PREPARATION OF SOLID PHASE SECOND ANTIBODY

A. Five grams of microcrystalline cellulose powder having a particle size up to 4 microns diameter (the small-size fraction of the product commercially available under the tradename Cellex MX) is added with vigorous agitation to a solution of 5 g. of cyanogen bromide (CNBr) in 200 ml. of distilled water, to which had been added gradually (i.e., dropwise) 1 N NaOH until a constant pH of 10.5 to 11.0 is obtained. For two minutes, the mixture is agitated with continued addition of 1 N. NaOH to maintain the pH in the range given above. The resulting slurry is filtered, the resulting activated cellulose washed with cold, distilled water, and if desired, dehydrated by treatment with increasing concentrations of acetone until 100% acetone is finally used.

B. The sheep anti-rabbit gamma globulin (for use as the second antibody) is precipitated in saturated (e.g., about 50%) aqueous ammonium sulfate solution and then 10 milligrams if the precipitate is dissolved in 5 ml. of 0.1 M NaHCO$_3$ (pH 8.5 – 9.0). Then 50 milligrams of the activated cellulose obtained in Part A. above is mixed in at room temperature and agitated therein for 24 hours. The cellulose-antibody conjugate is filtered, washed, and dehydrated.

In the following description, the lower case letter "u" is used (as a prefix to an abbreviation of a unit of measurement) instead of the Greek letter "$\mu$" to represent "micro".

EXAMPLE 2

For RIA determination of human placental lactogen (hPL), the following solutions, blood sera and solid phase second antibody conjugate, are used;

The solutions designated A., B., D., E., H., and the solid phase second antibody J. of Example 1 are used. In addition, the following are also used:

C'. A first antibody serum against hPL obtained from the blood serum of a rabbit that has been injected with hPL.

F'. A solution of the first antibody in C' above at a dilution of 1 part by volume per 1000 obtained by diluting 1 part of antibody solution C' above to 100 parts with Buffer B solution and then diluting 1 ml. of the resulting diluted solution with 9 ml. of the diluted solution obtained in E. above.

G'. A solution in Buffer A of hPL radioactively tagged by iodination with a radioactive iodine isotope, in this instance $^{125}$I. The $^{125}$I-hPL solution has a gamma ray radioactivity of 30,000 to 50,000 counts per minute.

I'. Human blood serum taken from a woman, especially one who is pregnant, whose hPL level is to be determined.

The assay procedure involves the following steps:

1. Dilute 10 ul of pregnancy serum I' with 2.0 ml of Buffer A.
2. Add 100 ul of diluted serum (obtained in Step 1) to a glass assay tube.
3. Add thereto 550 ul of Buffer A.
4. Add 50 ul of first antibody solution F'.
5. Add 100 ul of $^{125}$I hPL solution G' and vortex to mix.
6. Incubate 2 hours at room temperature.
7. Add 200 ul of a dispersion in Buffer A, of 32 mg. of solid phase second antibody J.
8. Incubate 30 minutes at 4° C.
9. Add 3 ml cold (4° C.) Buffer A solution.
10. Centrifuge cold (4° C.) at 1000X g for 2 minutes.
11. Decant supernatant and discard.
12. Count precipitate using a gamma counter.

If Step 7 used an antibody solution instead of the solid phase second antibody, the incubation in Step 8 would require a minimum of 12 hours.

EXAMPLE 3

For RIA determination of cortisol, the following solutions, blood sera and solid phase second antibody conjugate, are used;

The solutions designated A., B., D., E., H., and the solid phase second antibody J. of Example 1 are used. In addition, the following are also used:

C". A first antibody serum against cortisol obtained from the blood serum of a rabbit that has been injected with cortisol-BSA conjugate, i.e., the conjugate of cortisol with bovine serum albumin.

F". A solution of the first antibody in C" above at a dilution of 1 part by volume per 1000 obtained by diluting 1 part of antibody solution C" above to 100 parts with Buffer B solution and then diluting 1 ml. of the resulting diluted solution with 9 ml. of the diluted solution obtained in E. above.

G". A solution in Buffer A of cortisol-tyrosine methyl ester (TME) conjugate radioactively tagged by iodination with a radioactive iodine isotope, in this instance $^{125}$I. The $^{125}$I-cortisol-TME solution has a gamma ray radioactivity of 30,000 to 50,000 counts per minute.

I". Humam blood serum taken from a person whose cortisol level is to be determined.

The assay procedure involves the following steps:

1. Add 5 ul of human serum (obtained in Step I") to a glass assay tube.
2. Add thereto 200 ul of Buffer A. containing 0.8 mg. of subtilisin enzyme.
3. Incubate for 2 hrs. at 37° C.
4. Place in boiling water bath for 5 minutes; then cool to room temperature.
5. Add 100 ul of first antibody solution F".
6. Add 100 ul of $^{125}$I cortisol-TME solution G" and vortex to mix.
7. Incubate 1 hour at 37° C.
8. Add 200 ul of a dispersion, in Buffer A of 32 mg. of solid phase second antibody J.
9. Incubate 30 minutes at 4° C.
10. Add 3 ml. cold (4° C.) Buffer A solution.
11. Centrifuge cold (4° C.) at 1000X g for 30 minutes.
12. Decant supernatant and discard.
13. Count precipitate using a gamma counter.

If step 8 used an antibody solution instead of the solid phase second antibody, the incubation in Step 9 would require a minimum of 12 hours.

EXAMPLE 4

In the RIA determination of progesterone in human blood serum, there are used solutions, blood sera, and a solid phase second antibody analogous to those used in Example 3 except that the materials C", F", and G", are obtained using progesterone and its corresponding derivatives instead of cortisol. Reaction volumes in Steps 1. and 2. are increased because of the normally lower level of progesterone in the sera.

EXAMPLE 5

Example 3 is repeated except the $^{125}I$ is replaced by $^{131}I$ in Step G".

I claim:

1. In a method for determining the presence of an antigenic ligand in a body fluid suspected of containing the ligand comprising:
   1. mixing together an aqueous medium
      a. a sample of the body fluid;
      b. a corresponding antigenic ligand labeled with a radioactive isotope;
      c. a soluble antibody against the antigenic ligand immunogenically produced in an animal other than that from which the sample is obtained, and
      d. a second antibody against said soluble antibody immunogenically produced in an animal other than those which the sample and said soluble antibody are derived,
   2. incubating the resulting aqueous medium to allow the unlabeled ligand, if any, in (a) and labeled ligand (b) to competitively bind on said soluble antibody (c) and to cause mutual precipitation of antibodies of (c) and (d),
   3. separating the precipitated antibodies carrying bound ligand from the residual liquid medium containing free ligand, and
   4. subsequently measuring the radioactivity of the precipitated antibodies or of the residual liquid, or of both to determine the content of ligand in the sample, the improvement wherein said second antibody (d) is immobilized or insolubilized to a solid phase by polymerization with an aldehyde or alkyl haloformate; by physical entrapment in a gel polymer of an insoluble nature or by covalent coupling with a water-insoluble polymeric material or by adsorption on a water-insoluble polymeric material before it is added in step (1) above.

2. A method according to claim 1 wherein said second antibody is insolubilized by polymerization thereof with an insolubilizing agent.

3. A method according to claim 1 wherein said second antibody is immobilized by being physically entrapped in a gel polymer of insoluble nature.

4. A method according to claim 1 wherein said second antibody is insolubilized by covalent coupling with a water-insoluble polymeric material.

5. A method according to claim 1 wherein said second antibody is insolubilized by adsorption on a water-insoluble polymeric material.

6. A method according to claim 4 wherein the polymeric material is cellulose.

7. A method according to claim 2 wherein the insolubilizing agent is a lower alkyl chloroformate.

8. A method according to claim 3 wherein the insoluble polymer gel is a polymer of acrylamide with 1 to 10% by weight, based on the weight of acrylamide of a polyethylenically unsaturated monomer having at least two groups of the formula $H_2C = C <$.

9. A method according to claim 1 wherein the ligand to be assayed is human thyroid stimulating hormone.

10. A method according to claim 2 wherein the insolubilizing agent is ethyl chloroformate.

* * * * *